United States Patent [19]
Austin

[11] Patent Number: 5,360,017
[45] Date of Patent: Nov. 1, 1994

[54] ADJUSTABLE THERAPEUTIC PILLOW

[76] Inventor: David G. Austin, 5190 Brynwood Dr., Columbus, Ohio 43220

[21] Appl. No.: 67,583

[22] Filed: May 27, 1993

[51] Int. Cl.$^5$ .................... A61G 15/00; A47C 20/02
[52] U.S. Cl. .................................... 128/845; 5/640
[58] Field of Search ............... 128/845, 846, 882; 602/17, 18, 32, 35, 36; 5/636, 637, 640–645, 630, 643

[56] References Cited

U.S. PATENT DOCUMENTS

| | | | |
|---|---|---|---|
| 2,700,779 | 1/1955 | Tolkowsky | 5/636 |
| 3,140,497 | 7/1964 | Carswell | |
| 3,757,364 | 9/1973 | Downing | 5/636 |
| 3,795,021 | 3/1974 | Moniot | 5/636 |
| 3,828,377 | 8/1974 | Fary | |
| 3,981,032 | 9/1976 | Brooks | 5/636 |
| 4,235,472 | 11/1980 | Sparks | 5/630 |
| 4,259,757 | 4/1981 | Watson | 6/637 |
| 4,757,983 | 7/1988 | Ray | 5/637 |
| 4,850,067 | 7/1989 | Latorre | 5/639 |

*Primary Examiner*—Michael A. Brown
*Attorney, Agent, or Firm*—Thomas S. Baker, Jr.

[57] ABSTRACT

A therapeutic pillow assembly set is provided with interchangeable resilient neck-support components of different sizes, interchangeable resilient side-support components of different sizes, interchangeable resilient shoulder-support components of different sizes, and interchangeable resilient height-adjustment components of different sizes all of which are each selectively and detachably secured to a resilient base component by detachable-type fastener means.

17 Claims, 2 Drawing Sheets

ADJUSTABLE THERAPEUTIC PILLOW

FIELD OF THE INVENTION

This invention relates to pillows generally, and particularly concerns a pillow construction which readily permits convenient incremental pillow external configuration modification for pain relief as by an orthopedic therapist or prescribing physician.

BACKGROUND OF THE INVENTION

The use of pillow supports for the purpose of easing or relieving the pain experienced by patients in their neck and shoulder regions by reason of craniovertebral compression in a supine position is well known. U.S. Pat. No. 2,835,905 issued to Tomasson, for example, teaches an assembled pillow of relatively fixed external configuration. U.S. Pat. No. 2,940,088, issued in the name of Boos, also teaches a similarly configured pillow indicated to be useful for therapeutic purposes.

U.S. Pat. No. 3,140,497 issued to Carswell discloses a multi-piece pillow for use by sun bathers at a beach or lake, such pillow being provided with a recess which receives the user's face in a manner which facilitates face-down breathing. Two different multi-piece constructions for conventional, non-therapeutic pillows are disclosed by U.S. Pat. Nos. 3,239,854 and 3,403,414 issued in the names of Freedlander and Unger, respectively.

Greenawalt U.S. Pat. No. 3,521,310 discloses a unitary pillow construction using components of different firmness but not being readily detachable for replacement with other components to alter the pillows external shape for therapeutic purposes. U.S. Pat. No. 3,574,397 issued to Norries teaches a one-piece therapeutic pillow having the same limitations.

U.S. Pat. No. 3,828,377 issued to Fary, Sr. discloses a multi-piece body rest having chest and shoulder supports which may be moved laterally or longitudinally to accommodate corresponding body parts of a person in a face-down supine position. The Fary, Sr. apparatus also teaches a face support having recesses for the user's eyes and a notch for receiving the user's nose to facilitate breathing in the face-down position.

Lastly, Moore's U.S. Pat. No. 4,777,687 teaches a multi-piece apparatus for providing back and neck support, the apparatus having a pillow component of unitary, non-adjustable construction.

My invention overcomes the constructional and use constraints associated with the above-discussed pillow art by providing a pillow which may be custom fit to accommodate a patient's specific problem and is especially useful to orthopedic therapists and orthopedic physicians when prescribing and providing a course of treatment over time to reintroduce natural cervical curvature to the patient's neck and shoulder region.

SUMMARY OF THE INVENTION

To facilitate prescription activity by an orthopedic therapist or physician I provide a multi-piece pillow construction having modular neck-support, head-support, shoulder-support, height-adjustment, and base side-support, components which may be selected for particular size and then be detachably secured to the therapeutic pillow base unit through use of conventional loop and hook tape fastener elements previously secured to the different components. During the course of continuing prescription treatment the orthopedic therapist or physician can readily remove previously employed components from the base unit and replace those components with others of a different but desired size and/or shape thus changing the external configuration of the pillow to a form suitable for continued therapy. Also, the improved pillow of my invention may be advantageously used for pain management and therapeutic purposes.

Other advantages associated with my invention will become apparent from consideration of the drawings and detailed description which follow.

DETAILED DESCRIPTION

Figure 1:
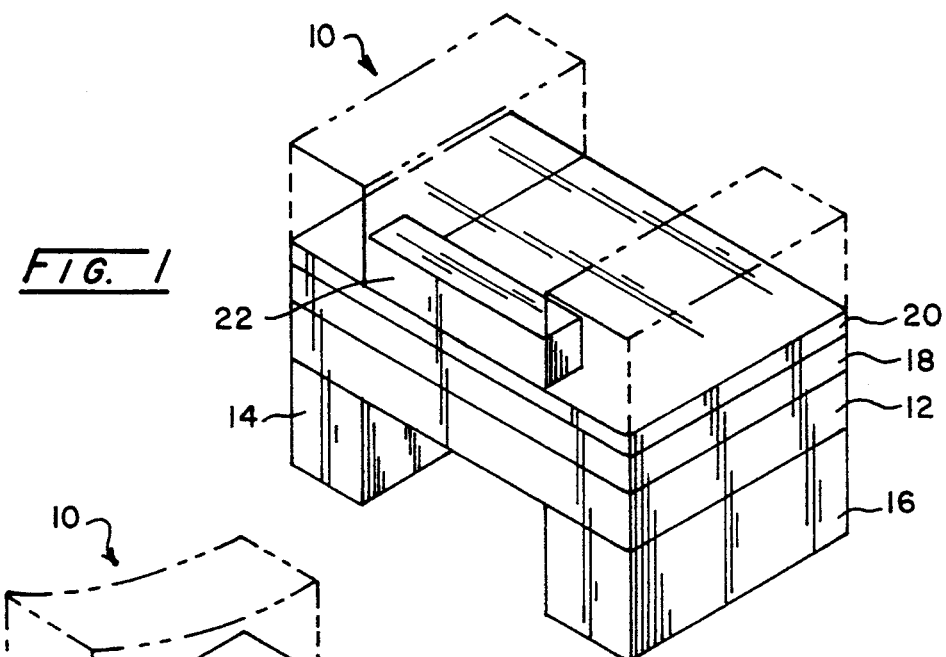
FIG. 1 is an isometric view of a preferred embodiment of the adjustable therapeutic pillow of my invention in its assembled condition.

FIG. 1 illustrates an assembly designated (10) which is a preferred embodiment of the adjustable therapeutic pillow of my invention. Assembly (10) is comprised of a base unit (12) in combination with detachable longitudinal base side-support components (14 and 16) secured to its under surface. These components also may be affixed to the top surface of base unit (12) as shown in phantom to immobilize a patient's head. Height-adjustment components (18 and 20), generally of same planform size as base unit (12), are detachably secured to base unit (12) and to each other. In addition, a neck support component (22) is removably attached to the upper surface of height-adjustment component (20).

For construction purposes I prefer that components (12 through 22) each be formed of a medium to high-density foamed hypoallergenic material such as foamed hypoallergenic polyurethane resin or a hypoallergenic polyester fiber. Typically the planform of base unit (12) is approximately 14" by 20" in size with a thickness usually of about 3". Height-adjustment components such as (18 and 20) may be of the same or different thicknesses depending upon the prescribing therapist's or physician's preference. Such components are typically made in modular or incremental thicknesses such as 1 inch, 2 inch, and 3 inch, and the desired components are selected from that assortment in any combination to give the desired overall assembly height adjustment.

Superimposed on the uppermost of height-adjustment components (18 and 20) in a readily detachable manner is the neck support component designated (22). Typically that component may have a circular, square, or even rounded-rectangular configuration depending on the preference of the prescribing professional. Usually a selection of sizes such as 1 ½ inch diameter, 2 ½ inch diameter, and 5 inch diameter, or comparable rectangular cross-section shape size, is provided for professional selection purposes. The preferred length for component (22) is generally about 10 inches.

Base support components (14 and 16) are also usually provided in a variety of sizes such as approximately 2 inches by 2 inches, 3 inches by 3 inches, and 5 inches by 5 inches in cross-section, and if necessary such may be combined in the manner that the height-adjustment components are combined. Also, such base unit support components are not to be restricted to square or even rectangular cross-sectional configurations.

Figure 2:
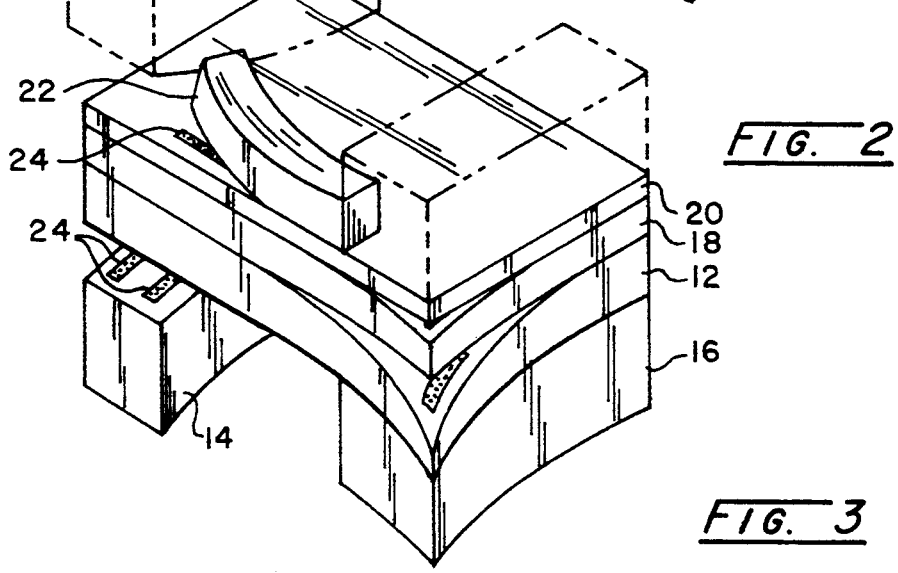
FIG. 2 is a similar view of the pillow assembly of FIG. 1 but in a partially exploded form to illustrate fastener elements utilized to readily detachably secure the different pillow components to the pillow base unit and to each other.

FIG. 2 in part illustrates the preferred use of loop and hook type fastener devices (24) for attaching the various components to each other in a readily and conveniently detachable manner. Such devices or fasteners are available in the industrial and domestic goods marketplaces and are often marketed under the trade-name "Velcro". It is preferred to attach the hook-type tapes and the loop-type tapes to the different components with a suitable contact-type adhesive, being assured that the various tape sections are properly positioned to that upon assembly the conjugate tape sections will adhere to each other.

Figure 3:
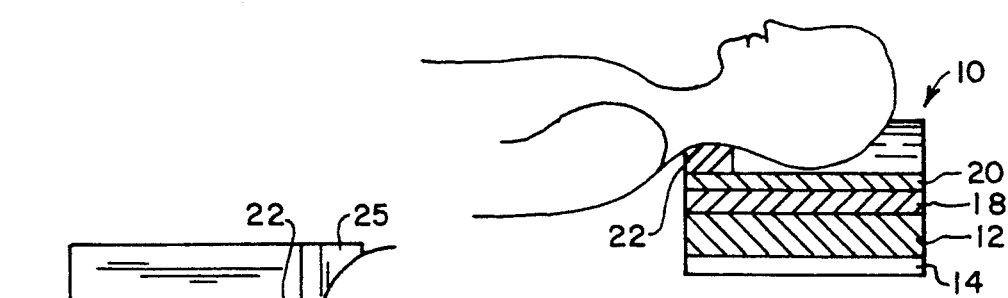
FIG. 3 is a sectional view of the assembly of FIGS. 1 and 2, but additionally illustrating the position of a patient's head and neck regions supported by the assembly when in a supine position.

As shown in FIG. 3, it is important to effect natural curvature of the patient's neck to alleviate pain in the supine position. When a patient has lost his/her natural lordotic curvature of the cervical vertebrae, increasing the height of the neck support component (22) by selecting and installing a larger-sized component will tend to restore that curvature over time in most cases.

Figure 4:
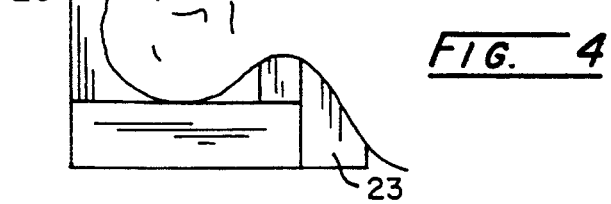
FIG. 4 is a view similar to FIG. 3 but in plan.
Figure 5:
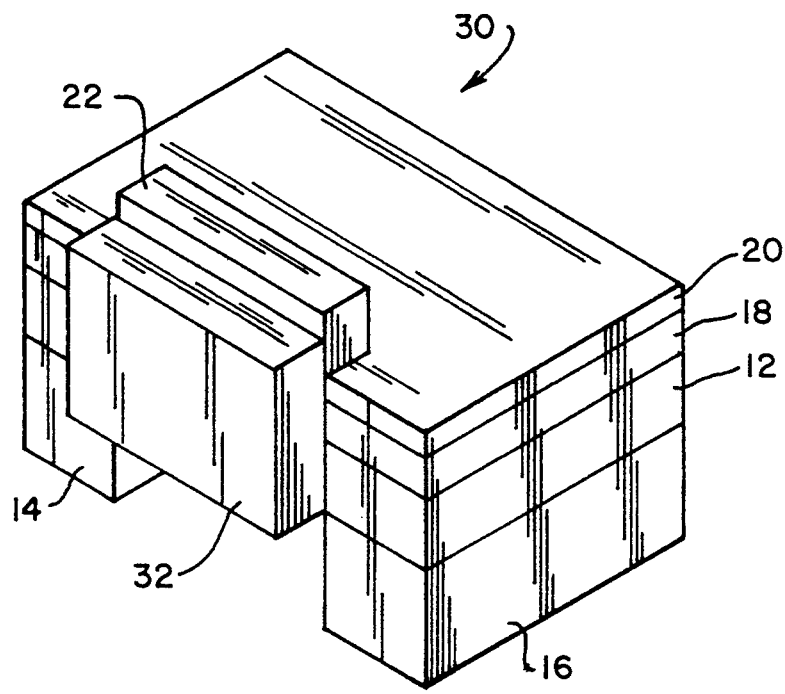
FIG. 5 is an isometric view of another embodiment of the adjustable therapeutic pillow of my invention in its assembled condition.

In many cases it is also desirable to impart a degree of longitudinal tractive force as between the patient's neck and shoulder regions to in effect push the shoulder axially away from the head and thereby decompress the affected cervical vertebrae and their associated musculature. Turning to FIG. 4, a pair of decompression inserts (23 and 25) are shown inserted between one edge of pillow (10) and top of a patient's shoulders. FIG. 5 illustrates another embodiment (30) of my invention which is additionally provided with a shoulder support component (32) that is removably secured to the axially-lower or near face of assembled components (12, 18, and 20). Hook and loop-type readily separable fastener tape sections are adhered to the engaged components for effecting such component attachment.

Figure 6:
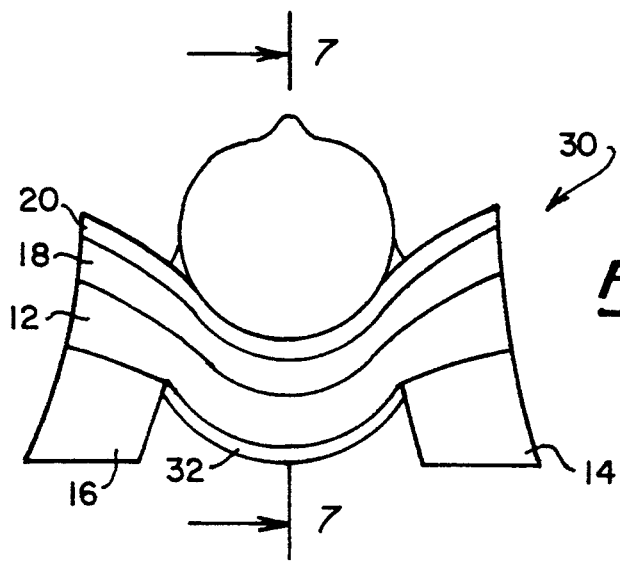
FIG. 6 is an elevational view of the assembly of FIG. 5 also illustrating the position of a patient's head supported by the assembly when in a supine position.
Figure 7:
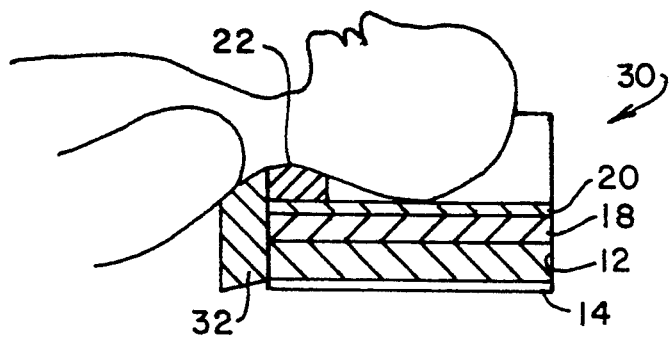
FIG. 7 is a sectional view of the assembly of FIGS. 5 and 6 additionally illustrating the position of a patient's head, neck, and shoulder regions supported by the assembly when in a supine position.

FIG. 6 illustrates the "cradling" effect for the patient's head that is achieved by the use of the separated base unit side-support components (14 and 16) attached to the underside of base unit (12). As shown in FIG. 7, the additional shoulder support component (32) provides shoulder support for the patient when in the supine position and functions to impart axial tractive forces which decompress the patient's craniovertebral complex.

Although not shown, assembly (10) or assembly (30) is preferably encased in a required fabric cover of 60 percent cotton–40 percent polyester.

From a method standpoint, it is necessary to periodically examine and consult with the patient to identify the progress that is being made during the course of remedial treatment. Depending upon the manifest symptoms, it may be necessary to change the size of the various neck-support, height-adjustment, base unit support, and shoulder support components (14 through 22 and 32), either upwards or downwards, to induce proper remedial treatment. Such may be readily accomplished by the prescribing therapist or physician through the ready removal and replacement of component parts and their convenient-to-use fastener devices.

Other materials, component shapes, and component sizes may be utilized in the practice of this invention.

I claim my invention as follows:

1. A therapeutic pillow assembly comprising:
   a resilient base component of substantially rectangular configuration having a topside surface, an underside surface, a pair of lateral side surfaces and a pair of longitudinal side surfaces;
   a resilient, adjustable neck-support component positioned upon and detachably secured to said base component topside surface and extending parallel to one of said lateral side surfaces; and
   said neck-support component being selected from a group of interchangeable neck-support components of different sizes.

2. The therapeutic pillow assembly defined by claim 1 and further comprising:
   a pair of resilient, independently adjustable side-support components positioned below and detachably secured to said base component underside surface;
   said pair of side-support components being selected from a group of interchangeable pairs of side-support components of different sizes.

3. The therapeutic pillow assembly defined by claim 2 and further comprised of:
   a resilient, adjustable height-adjustment component having a planform corresponding to the planform of said base component and being detachably secured to said base component topside surface;
   said height-adjustment component being selected from a group of interchangeable height-adjustment components of different sizes, and
   said neck-support component being detachably secured to said height-adjustment component instead of to said base component topside surface.

4. The Therapeutic pillow assembly defined by claim 3 and further comprised of:
   a resilient, adjustable shoulder-support component detachably secured to said base component at a base component edge defining the planform of said base component;
   said shoulder-support component being selected from a group of interchangeable shoulder-support components of different sizes.

5. The therapeutic pillow assembly defined by claim 1 and further comprised of:
   a resilient, adjustable shoulder-support component detachably secured to said base component at a base component edge defining the planform of said base component;
   said shoulder-support component being selected from a group of interchangeable shoulder-support components of different sizes.

6. The therapeutic pillow assembly defined by claim 1 and further comprising;
   a resilient, adjustable height-adjustment component having a planform corresponding to the planform of said base component and being supported by and detachably secured to said base component topside surface;

said height-adjustment component being selected from a group of interchangeable height-adjustment components of different sizes; and said neck-support component being detachably secured to said height-adjustment component instead of to said base-support component.

7. The therapeutic pillow assembly defined by claim 6 and further comprised of:

a resilient, adjustable shoulder-support component detachably secured to said base component at a base component edge defining the planform of said base component;

said shoulder-support component being selected from a group of interchangeable shoulder-support components of different sizes.

8. The therapeutic pillow assembly defined by claim 1 and further comprised of:

9. The therapeutic pillow assembly defined by claim 1 and further comprising:

a pair of resilient, adjustable side-support components positioned above and detachably secured to said base component topside surface;

said side support components being selected from a group of interchangeable pairs of side-support components of different sizes.

10. A therapeutic pillow assembly set comprising:

a resilient base component having a generally rectangular planform and having a topside surface, an underside surface, and a planform-defining surface that are each provided with at least one secured detachable-type fastener component, and a multiplicity of interchangeable resilient neck-support components of different sizes;

said neck-support components each being provided with at least one secured detachable-type fastener component that will cooperate with each corresponding detachable-type fastener component secured to said base component topside surface.

11. The therapeutic pillow assembly set defined by claim 10 and further comprising:

a multiplicity of interchangeable resilient side-support components of different sizes;

said side-support components each being provided with at least one secured detachable-type fastener component that will cooperate with each corresponding detachable-type fastener component secured to said base component underside surface.

12. The therapeutic pillow assembly set defined by claim 11 and further comprising:

a multiplicity of interchangeable resilient height-adjustment components of different sizes;

said height-adjustment components each being provided with a secured detachable-type fastener component that will cooperate with the detachable-type fastener component provided with said base component and with a secured detachable-type fastener component that will cooperate with the detachable-type fastener components provided with said neck-support components.

13. The therapeutic pillow assembly set defined by claim 12 and further comprising:

a multiplicity of interchangeable resilient shoulder-support components of different sizes;

said shoulder-support components each being provided with at least one detachable-type fastener component that will cooperate with a detachable-type fastener component secured to said base component at its planform-defining edge surface.

14. The therapeutic pillow assembly set defined by claim 11 and further comprising:

a multiplicity of interchangeable resilient shoulder-support components having different sizes;

said shoulder-support components each being provided with a secured detachable-type fastener component that will cooperate with the detachable-type fastener components provided with said base component at its planform-defining edge surface.

15. The therapeutic pillow assembly set defined by claim 10 and further comprising:

a multiplicity of interchangeable resilient height-adjustment components of different sizes;

said height-adjustment components each being provided with at least one secured detachable-type fastener component that will cooperate with the detachable-type fastener component provided on said base component and with at least one secured detachable-type fastener component that will cooperate with the detachable-type component secured to each of said neck-support components.

16. The therapeutic pillow assembly set defined by claim 12 and further comprising:

a multiplicity of interchangeable resilient shoulder-support components of different sizes;

said shoulder-support components each being provided with a secured detachable-type fastener component that will cooperate with the detachable-type fastener components secured to said base component at its planform-defining edge surface.

17. The therapeutic pillow assembly set defined by claim 10 and further comprising:

a multiplicity of interchangeable resilient shoulder-support components of different sizes;

said shoulder-support components each being provided with a secured detachable-type fastener component that will cooperate with the detachable-type fastener component provided with said base component at its planform-defining edge surface.

* * * * *